United States Patent [19]

Payton

[11] 3,996,378
[45] Dec. 7, 1976

[54] WATER-BASED MICROBICIDE FORMULATION
[75] Inventor: James H. Payton, Chicago, Ill.
[73] Assignee: Nalco Chemical Company, Oak Brook, Ill.
[22] Filed: July 30, 1975
[21] Appl. No.: 600,746

Related U.S. Application Data
[63] Continuation-in-part of Ser. No. 517,675, Oct. 24, 1974, abandoned.

[52] U.S. Cl. .............................. 424/302; 424/329; 424/361
[51] Int. Cl.² .......................................... A01N 9/18
[58] Field of Search ................... 424/302, 329, 361

[56] References Cited
UNITED STATES PATENTS

| | | | |
|---|---|---|---|
| 3,507,901 | 4/1970 | Matt et al. | 424/302 |
| 3,551,133 | 12/1970 | Sprayberry et al. | 424/361 |
| 3,560,390 | 2/1971 | Gaines | 424/329 |
| 3,717,452 | 2/1973 | Gibsen et al. | 71/117 |

Primary Examiner—V. D. Turner
Attorney, Agent, or Firm—John G. Premo; John S. Roberts

[57] ABSTRACT

Products and processes of a water-based formulation of methylene bis thiocyanate (MBT) in a xanthan gel, which is a hydrophilic colloid in water where the colloid is utilized at a concentration of about 0.02–2.0 weight percent and preferably 0.1–1.0 of the colloid carrier. In use in water treatment, this dosage is adjusted so that use dosage contains about 2–1000 ppm by weight of the microbicide and preferably 20–200 ppm. Alternatively, a ternary formulation may be used containing methylene bis thiocyanate plus an auxiliary fast-acting biocide in the same xanthan gel. The auxiliary microbicide is selected from an n-alkyl ($C_{12}$–$C_{18}$) dimethyl(benzyl)ammonium chloride such as the preferred quaternary; i.e., tetradecyl benzyl dimethyl ammonium chloride (ROCCAL-MC-14—Hilton-Davis). The methylene bis thiocyanate or combination of microbicides is utilized for shipment or make up concentration in a weight percentile of 5–20%; a preferred percentile of 5–10%; and an optimum percentile of about 10%, based upon the xanthan carrier in water. The critical microbicide particle size, which is slightly greater than colloidal, is in the broad range 0.8–150 microns, with a preferred average particle size of 1–45 microns.

4 Claims, No Drawings

WATER-BASED MICROBICIDE FORMULATION

The present invention relates to improved methods of formulating composition containing methylene bis thiocyanate with or without an auxiliary fast-acting quaternary microbicide. Such compositions industrially are useful in water treatment and active against bacteria, fungi, etc. As has been the problem elsewhere with medicines and broad spectrum fungicides, bactericides, unrelated or unwanted toxicity has developed in some cases due to the organic carrier or diluent used. Additionally, in shipping, the use of conventional aromatic diluents such as benzene, toluene, and xylene interpose flammability as well as health hazards in themselves.

PRIOR ART

Illustrative of prior patent art:

The production of methylene bis thiocyanate in an organic medium:

U.S. Pat. No. 3,524,872 Matt (Nalco) - Utilizing an organic solvent of limited miscibility; e.g., toluene and water where the organic solvent is toluene in the reaction and later crystallized in the presence of a water-miscible organic solvent and water.

Canadian Pat. No. 763,971 Kawanami et al, (Sumitomo) - Production of methylene bis thiocyanate in aqueous with an organic water-soluble solvent added.

The use of xanthan:

British Pat. No. 1,160,675 Gibson et al, - Utilization of a xanthan colloid in water to cause better adherence of a herbicide to the treated area. U.S. Pat. No. 3,326,733 Colegrove - Utilization of xanthan (Xanthomonas campestris) as a carrier for an explosive. U.S. Pat. No. 3,717,452 Gibson et al - Related to British '674 above and vectored to spray coating plants utilizing xanthan gel with an active agent to form a treating agent termed "an agricultural chemical." U.S. Pat. No. 3,659,026 Schuppner (Kelso Co.) - This patent, cited in the parent of the present application, relates to a combination of Xanthomonas colloid and locust bean gum utilized as a carrier for agricultural chemical. U.S. Pat. No. 3,507,901 Mat et al. (Nalco) - Additionally cited in the parent of the present application, this patent relates to the synthesis of methylene bis thiocyanate under aqueous conditions. There is no definition or disclosure of critical particle size or its inclusion into a Xanthan gel.

The present formulations, as opposed to those containing methylene bis thiocyanate and an organic carrier or diluent for use, are water-based formulations of methylene bis thiocyanate which comprise small methylene bis thiocyanate particles in a range of about 0.8–150 microns in a xanthan gel wherein the weight percent in methylene bis thiocyanate in shipment is 5–20 and preferably 5–10 and an optimum of about 10% of the xanthan gum or gel. In use the dosage is adjusted so that about 2–1000 ppm by weight of the microbicide is actually used in water treatment, and preferably 20–200 ppm. These formulations also may encompass the use of a fast-acting auxiliary biocide or slimicide which is a quaternary compound and specifically is a long chain ($C_{12}$–$C_{18}$) dimethyl benzyl ammonium chloride, such as ROCCAL MC-14 (Hilton-Davis) where C = 14 in the formula above. To the water-based formulation of xanthan which contains 0.02–2.0% by weight of xanthan hydrophilic colloid is added methylene bis thiocyanate or methylene bis thiocyanate plus the quaternary. The colloid in water may be viewed as an aqueous carrier and the combination is a thick suspension.

It has been long known that methylene bis thiocyanate formulations break down into degradation products which release HCN. It has been found that in the present water-based formulations there is less cyanide release than in those where methylene bis thiocyanate is used with an organic carrier.

METHYLENE BIS THIOCYANATE

During the past decade the compound methylene bis thiocyanate proved commercially popular and successful for water-treatment purposes and this is the subject of many patents, a sampling of which is noted above. Objections have been raised, however, due to the fact that the shipment and treatment carriers for methylene bis thiocyanate have in some cases proved troublesome due to toxicity and flammability. In addition, where specialized uses involving microbial-contaminated bodies of water which may be natural or artificial and flowing as in cooling towers, the relatively slow-acting nature of methylene bis thiocyanate as a microbicide has posed some problems. In order to eliminate organic diluents such as benzene, toluene, and xylene, which are commercially popular but toxic as well as flammable, the present invention proposes a different solution.

In this invention a water-based formulation is utilized and in order to disperse the methylene bis thiocyanate particles in the preferred carrier, the particles are reduced in size to a range with a broad average particle size of 0.8–150 microns and a preferred average particle size of 1–45 microns.

The necessary and critical reduction of size of the methylene bis thiocyanate particles is brought about in two ways: (a) in a colloid mill and (b) in a piston homogenizer.

Similar reduction in size for any additional starting materials is also affected by the above routes.

XANTHAN GUM

Xanthan gum is a high molecular weight natural carbohydrate, or more specifically polysaccharide. The generic term xanthan gum defines exocellular biopolysaccharides which are produced in a pure culture fermentation process by the microorganism Xanthomonas campestris.

The water-soluble Xanthomonas campestris hydrophilic colloid herbicide solution so produced while considerably thicker than water will have a viscosity within the exemplary range of 400 to 1,200 centipoises. Such a solution surprisingly is easily pumpable with equipment used in the commercial application of water chemicals.

By structure this colloidal material is a polymer containing mannose, glucose, potassium, glucuronate and acetyl radicals. Other Xanthomonas colloidal material may also be used and these are produced by substituting known Xanthomanas bacteria or organisms; i.e., Xanthomonas carotae, Xanthomonas incanae, Xanthomonas begoniae, and Xanthomonas malvacearum, for the bacterium Xanthomonas campestris.

The xanthan gum solutions among other features are remarkably stable to the addition of salts and also exhibit a property known as pseudoplastic; i.e., when shear stress is applied, viscosity is reduced in proportion to the amount of shear and upon the release of shear, total viscosity recovery occurs almost instantaneously. These xanthan gums are available commercially as KELZAN, and product of Kelco Company, San Diego, Calif.

In the application of the preferred colloid KELZAN, the utilization of this colloid was found to be specific in that the following other thickeners or carriers were found not suitable: carboxy methyl cellulose, hydroxy ethyl cellulose, guar gum, hydroxy propyl cellulose, carboxyl and sodium alginate.

THE QUATERNARY

To counteract the relative slow action of methylene bis thiocyanate, an additive microbicide is utilized in the ternary forms of the present invention. This auxiliary microbicide is a fast-acting slimicide or bactericide which is selected from a long chain ($C_{12}$–$C_{18}$) dimethyl benzyl ammonium chloride. A specific preferred auxiliary microbicide is tetradecyl benzyl dimethyl ammonium chloride (ROCCAL-MC-14 — Hilton-Davis, Cincinnati, Ohio). This auxiliary agent is compatible with methylene bis thiocyanate and when the combination microbicide is utilized, the dosage concentration is selected so that the amount of quaternary utilized substitutes for a portion of the methylene bis thiocyanate as described above. Since the activity of the quaternary against many common microorganisms is roughly equivalent to methylene bis thiocyanate, this substitution is convenient and facile. The weight percent relationship of methylene bis thiocyanate:quaternary may be within the ranges of 10:1 to 1:10 and a preferred formulation utilizes a relation of 2:1 of methylene bis thiocyanate to quaternary. ROCCAL-MC-14 has a broad range germicidal action and has been found effective against the following representative microbial agents: *Enterobacter aerogenes, Escherichia coli, Salmonella typhosa, Salmonella choleraesuis, Salmonella schottmuelleri, Pseudomonas aeruginosa, Shigella dysenteriae, Staphylococcus aureus,* and *Streptococcus faecalis.*

EXAMPLE 1

In Table I, samples 151-156, inclusive, show satisfactory pumping rates, a necessary adjective quality with the present compositions. These samples also showed particle size distribution between 150 and 0.8 $\mu$; conversely, in the table, samples 147–150 show reduced or no pumping rate and show substantial particle size distribution in the average range of 180–420 $\mu$.

Pumping rates were determined for each of the experimental batches using two different chemical feed pumps. Anything less than the maximum pumping rate indicates that the action of the check valves in the pump is being inhibited by particles. The particles hold the check valves open and allow some backflow. Experience has shown that eventually the build up of these large particles around the check valves will cause the pump to stop functioning entirely.

The particle size data was run using a standard set of sieves. A Millipore filter with 5 $\mu$ pores (0.8 in two examples) was used as the smallest "sieve." Particle sizes below 1 micron are almost impossible to determine. This is the lower limit for identification with a light microscope. Scanning electron microscopic sizing is not possible because the particles are organic and would tend to sublime in the high vacuum required. An optical microscope with a dark field attachment confirmed that there were a large number of very small particles (smaller than 1 micron) in the Millipore filtrate, but sizing is not possible using dark field techniques.

TABLE I

PARTICLE SIZE DATA - WATER BASED METHYLENE BIS THIOCYANATE
% Methylene Bis Thiocyanate Particle Trapped on Various Sieves

| Sample | Precision Preparation Method | Pump Rate[a] A&F ml/min. | Pump Rate[b] ml/min. | 420$\mu$ | 250$\mu$ | 180$\mu$ | 150$\mu$ | 90$\mu$ | 60$\mu$ | 45$\mu$ | 20$\mu$ | Smaller 5$\mu$[c] | than 5$\mu$ |
|---|---|---|---|---|---|---|---|---|---|---|---|---|---|
| 147 | Colloid Mill .040" gap | won't pump | won't pump | 27.5 | 27.4 | 9.9 | 3.0 | 1.8 | 2.0 | 0.5 | 0.3 | 14.2[d] | 13.5[e] |
| 148 | Colloid Mill .012" gap | 14.0 | 7.0 | 6.2 | 40.4 | 12.7 | 3.0 | 2.6 | 0.8 | 0.8 | 0.1 | 3.5 | 29.8 |
| 149 | Colloid Mill .007" gap | 25.0 | 25.0 | 0.1 | 9.3 | 19.2 | 4.0 | 6.1 | 35.6 | 11.1 | 3.9 | 9.5 | 1.2 |
| 150 | Colloid Mill .0035" gap | 29.0 | 28.0 | 0.5 | 0.5 | 3.1 | 2.2 | 6.7 | 7.6 | 15.2 | 4.4 | 8.9 | 50.7 |
| 151 | Colloid Mill .0025" gap | 30.6 | 30.0 | 0.0 | 0.0 | 0.0 | 0.0 | 5.0 | 6.3 | 3.5 | 9.8 | 7.3 | 68.1 |
| 152 | Colloid Mill .0015" gap | 31.0 | 31.0 | 0.0 | 0.0 | 0.0 | 0.0 | 1.0 | 1.0 | 1.4 | 6.1 | 5.9 | 85.6 |
| 153 | Colloid Mill .0005" gap | 31.0 | 31.0 | 0.0 | 0.0 | 0.0 | 0.0 | 0.0 | 0.6 | 0.4 | 0.1 | 6.4 | 92.5 |
| 154 | Homogenizer 2000 | 31.0 | 31.0 | 0.0 | 0.0 | 0.0 | 0.0 | 0.4 | 2.4 | 0.7 | 1.4 | 8.2[d] | 86.7[e] |
| 155 | Homogenizer 6000 psi | 31.0 | 31.0 | 0.0 | 0.0 | 0.0 | 0.0 | 0.0 | 0.4 | 0.3 | 0.9 | 6.0 | 92.3 |
| 156 | Plant Batch, 10% Methylene bis thiocyanate aqueous | 31.0 | 31.0 | 0.0 | 0.0 | 0.0 | 0.0 | 1.7 | 3.3 | 0.0 | 3.7 | 7.9 | 83.5 |
| | Kelzan + Water 9000 cps | 31.0 | 31.0 | | | | | | | | | | |

(Average pumping rate over a 5-minute period)

[a] Precision Pump-Model 12721-11
[b] A&F Pump-Model VW 8A-658-3
[c] 5$\mu$ Millipore Filter
[d] 0.8$\mu$ Millipore Filter
[e] Smaller than 0.8$\mu$

EXAMPLE 2

Four-day static fish toxicity studies wherein a 10% dispersion of methylene bis thiocyanate in xanthan gel utilizing piston homogenizer with effective particle size largely concentrated in the 1–45 micron range are shown in Table II.

The results appear to show a lesser toxicity toward the trout than bluegill and the compositions show a toxicity for both fish greater than 1.0 ppm and less than 10.0 ppm.

TABLE II

Results of Four-Day Static Fish Toxicity Study
Rainbow Trout and Bluegills

| Dose Level (ppm) | Parameter | Rainbow Trout Elapsed Time (hours) | | | | | | Bluegills Elapsed Time (hours) | | | | | |
|---|---|---|---|---|---|---|---|---|---|---|---|---|---|
| | | 1–6 | 24 | 48 | 72 | 96 | Total | 1–6 | 24 | 48 | 72 | 96 | Total |
| 1,000 | pH | 5.6 | — | — | — | — | — | 5.4 | — | — | — | — | — |
| | DO | 9.1 | — | — | — | — | — | 8.8 | — | — | — | — | — |
| | °C | 12.6 | — | — | — | — | — | 18.4 | — | — | — | — | — |
| | Survivors | 0 | 0 | 0 | 0 | 0 | 0% | 0 | 0 | & 0 | 0 | 0 | 0% |
| 100 | pH | 6.7 | — | — | — | — | — | 6.4 | & 6.6 | & — | — | — | — |
| | DO | 8.6 | — | — | — | — | — | 8.2 | 9.3 | — | — | — | — |
| | °C | 12.6 | — | — | — | — | — | 18.4 | 18.0 | — | — | — | — |
| | Survivors | 0 | 0 | 0 | 0 | 0 | 0% | 4 | 0 | & 0 | 0 | 0 | 0% |
| 10 | pH | & — | & 6.5 | — | — | — | — | — | 6.5 | 6.5 | — | — | — |
| | DO | — | 8.2 | — | — | — | — | — | 8.5 | 8.8 | — | — | — |
| | °C | — | 12.8 | — | — | — | — | — | 18.0 | 18.0 | — | — | — |
| | Survivors | & 10 | 10 | 0 | 0 | 0 | 0% | & 10 | 1 | 0 | 0 | 0 | 0% |
| 1 | pH | & — | & — | — | — | — | — | & — | & — | & — | & 6.8 | — | — |
| | DO | — | — | — | — | — | — | — | — | — | 6.5 | — | — |
| | °C | — | — | — | — | — | — | — | — | — | 18.0 | — | — |
| | Survivors | 10 | & 10 | 10 | 10 | 10 | 100% | & 10 | & 10 | & 10 | 9 | 9 | 90% |

Four-Day $TL_{50}$  >1.0 ppm  <10.0 ppm  >1.0 ppm  <10.0 ppm

EXAMPLE 3

Methylene Bis Thiocyanate Formulation

The following materials were reduced in a colloid mill and it was found after one run that the material was improved when the KELZAN and water were blended first and then the acid and methylene bis thiocyanate added afterward.

| | Wt. % |
|---|---|
| Water | 86.2 |
| KELZAN | 0.8 |
| 90% Formic Acid | 3.0 |
| Methylene bis thiocyanate | 10.0 |

EXAMPLE 4

Microbicidal Activity of Aqueous Methylene Bis Thiocyanate Composition

In the following example, a so-called KIM test is set out which is a preliminary test for fungi and bacteria. Also a comparison is made in the B section between a 10% methylene bis thiocyanate product aqueous versus a corresponding 10% methylene bis thiocyanate product organic solvent.

Further experiments showed that the use dosage range countered and used with products of this type is from about 2–1000 ppm with a preferred range of from 20–200 ppm of the microbicide.

A. KIM Tests

| | | Test Bacteria 48 Hr. Inhibition | Test Fungi 5 Day Inhibition |
|---|---|---|---|
| Aqueous This Invention | pH 5 | 2.5/5 | 2.5/5 |
| | pH 7 | 5/10 | 10/25 |
| Organic Solvent | pH 5 | 2.5/5 | 5/10 |

-continued

A. KIM Tests

| | Test Bacteria 48 Hr. Inhibition | Test Fungi 5 Day Inhibition |
|---|---|---|
| pH 7 | 5/10 | 25/50 |

5/10 means that some dosage between 5 and 10 ppm is the minimum inhibiting dosage. The sample at 5 ppm showed some microbiological growth while there was no growth at 10 ppm.

The test bacteria and fungi utilized were those of a standard ASTM procedure; namely, *Aerobacter aerogenes*, ATCC 13048, for the bacteria test organism, and *Aspergillus niger*, ATCC 6275, for the fungus test organism.

B. Comparison Tests

The following tests were run on microbiologically contaminated pulp slurries made in the laboratory. The samples were treated with given dosages of a biocide and samples were withdrawn at the stated time intervals. Counts of total aerobic bacteria and total fungi were determined by ASTM methods and the results were compared with an untreated control sample to determine the percent reduction in microbiological populations.

| Treatment | Dosage (ppm) | % Reduction Bacteria | | % Reduction Fungi | |
|---|---|---|---|---|---|
| | | 4 hr. | 24 hr. | 4 hr. | 24 hr. |
| pH 6.5 | | | | | |
| Organic base methylene bis thiocyanate formulation | 10 | | | 0 | 0 |
| | 25 | | | 0 | 0 |
| | 50 | | | 90 | 99.96 |
| | 100 | | | 99.96 | 99.96 |
| Water or aqueous based methylene bis thiocyanate formulation | 10 | | | 0 | 0 |
| | 25 | | | 90 | 95 |
| | 50 | | | 99.95 | 99.95 |
| | 100 | | | 99.95 | 99.95 |
| pH 7.5 | | | | | |
| Organic base methylene bis thiocyanate formulation | 50 | 55 | 12 | | |
| | 100 | 94 | 33 | | |
| | 250 | 94 | 33 | | |
| Water or | 50 | 95 | 75 | | |

-continued

| Treatment | Dosage (ppm) | % Reduction Bacteria | | % Reduction Fungi | |
|---|---|---|---|---|---|
| | | 4 hr. | 24 hr. | 4 hr. | 24 hr. |
| aqueous based methylene bis thiocyanate formulation | 100 | 99.3 | 99.92 | | |
| | 250 | 99.8 | 99.98 | | |

In the above experiments the water-based formulation of methylene bis thiocyanate gives increased fungicidal activity as well as better activity against bacteria in higher pH systems.

I claim:

1. In a water-based microbicide composition comprising methylene bis thiocyanate and a xanthan gel carrier, the improvement comprising utilizing a dispersion of methylene bis thiocyanate with a particle size of 0.8–150 microns in a xanthan gel carrier wherein the methylene bis thiocyanate is about 5–20% of the xanthan gel and wherein said formulation possesses superior safety attributes of less toxicity and less flammability over organic solvent based compositions.

2. The microbicide composition according to claim 1 further comprising an effective amount of a fast-acting quaternary biocide which is $C_{14}$ dimethyl benzyl ammonium chloride.

3. In a method of treating microbial-contaminated water which comprises incorporating therein at least an antimicrobial amount of a formulation consisting of methylene bis thiocyanate and a carrier, the improvement comprising the use of methylene bis thiocyanate in a particle size of 0.8–150 microns in a xanthan gel carrier where the make up weight percent of methylene bis thiocyanate is about 5–20 of the xanthan gel in water and wherein said formulation is applied in a dosage range of 2–1000 ppm of methylene bis thiocyanate and possesses superior safety attributes of less toxicity and less flammability.

4. The method according to claim 3 further comprising effective amount of $C_{14}$ dimethyl benzyl ammonium chloride.

* * * * *